United States Patent [19]

Haugland et al.

[11] Patent Number: 4,774,339

[45] Date of Patent: Sep. 27, 1988

[54] CHEMICALLY REACTIVE DIPYRROMETHENEBORON DIFLUORIDE DYES

[75] Inventors: Richard P. Haugland, Junction City; Hee C. Kang, Eugene, both of Oreg.

[73] Assignee: Molecular Probes, Inc., Eugene, Oreg.

[21] Appl. No.: 83,458

[22] Filed: Aug. 10, 1987

[51] Int. Cl.⁴ .................. C07D 209/00; C07D 209/56
[52] U.S. Cl. .................................................. 548/405
[58] Field of Search .................... 564/11, 10; 260/349, 260/549; 548/545, 405

[56] References Cited

U.S. PATENT DOCUMENTS

| | | | |
|---|---|---|---|
| 3,135,789 | 6/1964 | Fried et al. | 564/10 X |
| 3,201,464 | 8/1965 | Brown et al. | 564/10 |
| 3,336,380 | 8/1967 | Muetterties | 564/11 X |

*Primary Examiner*—Paul F. Shaver

[57] ABSTRACT

Novel fluorescent dyes based on the dipyrrometheneboron difluoride structure are provided. The new reagents contain functional groups capable of forming a stable fluorescent product with functional groups typically found in biomolecules or polymers including amines, phenols, thiols, acids, aldehydes and ketones. Reactive groups in the dipyrrometheneboron difluoride dyes include activated esters, isocyanates, amines, hydrazines, sulfonyl halides, acids, aldehydes, alcohols and haloacetamides. The products are detected by their absorbance or fluorescence properties. The spectral properties of the fluorescent dyes are sufficiently similar in wavelengths and intensity to fluorescein as to permit use of the same euqipment. The dyes, however, have narrower spectral bandwidths than fluorescein, do not show appreciable sensitivity to pH, have higher solubility in non-polar solvents and have improved photostability.

13 Claims, 2 Drawing Sheets

Figure 1:
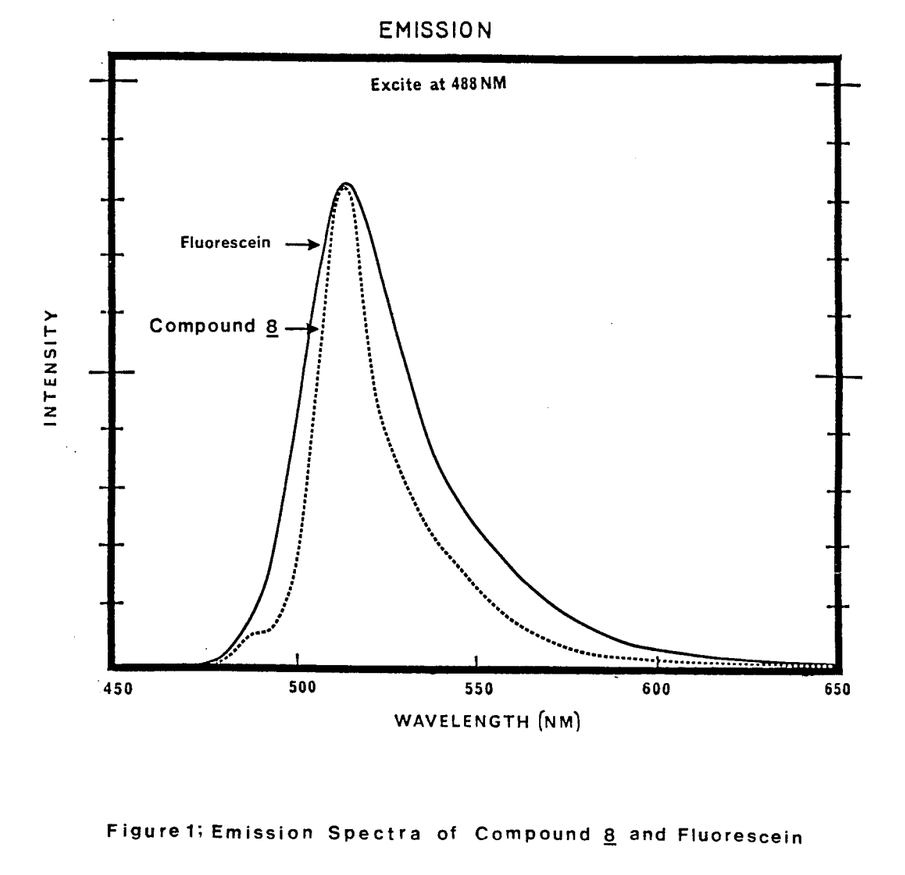

Figure 1: Emission Spectra of Compound 8 and Fluorescein

Figure 2:
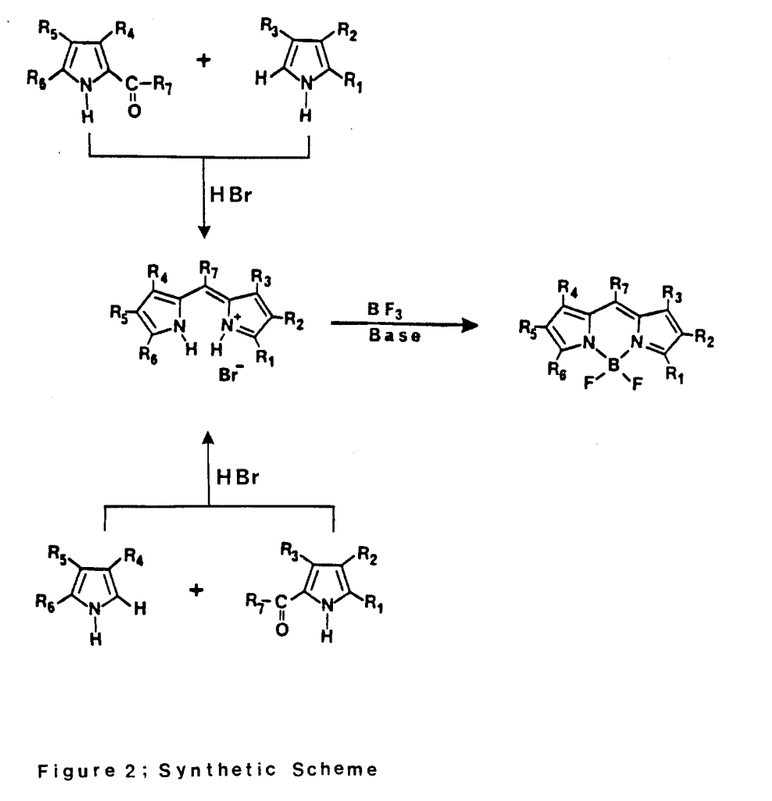

Figure 2; Synthetic Scheme

CHEMICALLY REACTIVE DIPYRROMETHENEBORON DIFLUORIDE DYES

FIELD OF THE INVENTION

This invention is related to improvements in dyes useful as fluorescent tracers. Specifically the improvements relate to chemically reactive dyes that can be attached to ligands with fluorescence properties sufficiently similar to fluorescein dyes so that the same equipment can be used but with unique spectral and chemical advantages.

BACKGROUND OF THE INVENTION

Fluorescent dyes are widely used as tracers for localization of biological structures by fluorescence microscopy, for quantitation of analytes by fluorescence immunoassay, for flow cytometric analysis of cells, for measurement of physiological state of cells and other applications [Kanaoka (1977); Hemmila (1985)]. Their primary advantages over other types of absorption dyes include the visibility of emission at a wavelength distinct from the excitation, the orders of magnitude greater detectability of fluorescence emission over light absorption, the generally low level of fluorescence background in most biological samples and the measurable intrinsic spectral properties of fluorescence polarization [Jolley, et al. (1981)], lifetime and excited state energy transfer (U.S. Pat. No. 3,996,345).

For many applications that utilize fluorescent dyes as tracers, it is necessary to chemically react the dye with a biologically active ligand such as a cell, tissue, protein, antibody, enzyme, drug, hormone, nucleotide, nucleic acid, polysaccharide, lipid or other biomolecule to make a fluorescent ligand analog or with natural or synthetic polymers. With these synthetic probes the biomolecule frequently confers a specificity to a biochemical interaction that is to be observed and the fluorescent dye provides the method for detection and/or quantitation of the interaction. Chemically reactive synthetic fluorescent dyes have long been recognized as essential for following these interactions [Soini and Hemmila, 1979]. The dyes in common use are limited to a relatively small number of aromatic structures. It is the object of this invention to provide improved fluorescent dyes. It is further an object of this invention to provide dyes with the chemical reactivity necessary for conjugation to the functional groups commonly found in biomolecules, drugs, and natural and synthetic polymers.

Coons and Kaplan in 1950 first prepared a chemically reactive isocyanate of fluorescein and later Riggs, et al. (1958) introduced the more stable isothiocyanate analog of fluorescein. Fluorescein isothiocyanate (FITC) remains one of the most widely used tracers for fluorescent staining and immunoassay. Other reactive fluoresceins were prepared by Haugland (U.S. Pat. No. 4,213,904). Virtually all fluorescence microscopes are equipped with excitation sources and filters optimized to excite and detect fluorescein emission. Due to the intense but discrete excitation of the argon laser at 488 nm which is strongly absorbed by the primary fluorescein absorption band (maximum at 492 nm), fluorescein has also become the primary dye for use in the technique of flow cytometry [Lanier & Loken (1984)].

The primary advantages that have permitted fluorescein isothiocyanate and its conjugates to remain the standard for microscopy and fluorescence immunoassay are a high absorbance, a high quantum yield and general ease of conjugation to biomolecules. The only fluorescent tracers in common use that exceed the overall fluorescence yield on a molar basis are the phycobiliproteins [U.S. Pat. No. 4,520,110; Oi, et al (1983), Kronick (1983)]. These require special methods for conjugate to biomolecules and in some cases such as fluorescence polarization immunoassays [Jolley, et al. (1981)] have too high a molecular weight to be useful. They also have high susceptibility to photodegradation. The only chemically reactive fluorophores with similar spectra to fluorescein that have been described are derived from the nitrofurazan structure [Soini and Hemilla (1979)]. These fluorophores have much weaker absorptivity (less than 25,000 cm$^{-1}$ M$^{-1}$ at its peak at 468 NM versus 75,000 cm$^{-1}$ M$^{-1}$ for fluorescein at its peak near 490 NM) and virtually no fluorescence in aqueous solutions where fluorescein is usually used and where most applications in immunofluorescence exist.

Despite their widespread acceptance as fluorescent tracers, fluorescein tracers have some deficiencies that preclude or make more difficult some useful applications. Primary is the strong tendency of the fluorophore to photobleach when illuminated by a strong excitation source such as the lamp used in fluorescence microscopes. The photobleaching can result in a significant percentage of the fluorescence being lost within seconds of the onset of illumination. In fluorescence microscopy this results in loss of the image. In fluorescence assays, the loss of fluorescence with time makes quantitation of results more difficult and ultimately decreases the sensitivity of detection of the analyte. To a variable degree, extrinsic reagents including propyl gallate and p-phenylenediamine retard but do not eliminate the photobleaching. Additionally, fluorescein shows a pH dependent absorption spectrum which decreases the fluorescence yield in solutions at a physiological pH or below. Furthermore, the emission spectrum of fluorescein has a very broad long wavelength component which greatly increases its background at wavelengths used for detection of other dyes such as rhodamine B in applications such as DNA sequencing [L. M. Smith, et al. (1986)] and flow cytometry that require detection of multiple dyes. Due to the chemical nature of fluorescein, all of its fluorescent derivatives have an ionic charge. The ionic charge and general lack of solubility in non-polar solvents preclude its use as a fluorescent tracer for lipophilic structures and decrease its suitability or such applications as a chromatographic derivatization reagent.

SUMMARY OF THE INVENTION

No fluorescent tracers have previously been described with the combination of fluorescein-like spectra, chemical reactivity with the functional groups typically combined with fluorescent tracers, lack of pH sensitivity of spectra, narrow emission band-width and solubility in non-polar environments. The subject materials of this invention have fluorescence properties sufficiently similar to fluorescein that they can use the same optical equipment as used with fluorescein-based tracers without modification of the excitation sources or optical filters. In some cases they show significantly higher photostability than fluorescein without addition of external stabilizing agents. They show low sensitivity of fluorescence emission to pH and solvent and have emission yields comparable to fluorescein. The emission band-width is unusually narrow. Some of the reactive derivatives lack ionic charge and their conjugates have a broad range of solubility including non-polar solvents.

DESCRIPTION OF SPECIFIC EMBODIMENTS

The base for the improved photostable fluorophores is a new dipyrrometheneboron difluoride compound. The parent heterocyclic compound was first synthesized by Vos de Waal, et al (1977) and its fluorescence properties subsequently described by Wories, et al (1985). Their research did not provide methods whereby the fluorophores could be chemically reacted with ligands. This invention describes novel methods for synthesis of reactive derivatives of this fluorophore and demonstration that the materials can be chemically bonded to the functional groups present in many biomolecules to form fluorescent ligand analogs or polymeric materials for use as fluorescent tracers. Potentially reactive functional groups intrinsically present or that can be introduced into biomolecules and polymers include but are not limited to amines, thiols, alcohols, carboxylic acids, aldehydes, and ketones. Chemically reactive fluorescent reagents have been developed in this invention for modification of all of these functional groups under conditions of solvent, temperature and pH that usually do not destroy the biological activity of the modified biomolecule. None of the reagents previously described in the chemical or biochemical literature are recognized as possessing the appropriate combination of chemical reactivity, spectra, photostability, fluorescence yield and lack of pH sensitivity to make them suitable alternatives to flurescein.

The new derivatives of the dipyrrometheneboron difluoride heterocycle that are the subject of this invention have the general structure below.

In this structure, $R_1$, $R_2$, $R_3$, $R_4$, $R_5$, and $R_6$ are chosen among the substituents hydrogen, halogen, alkyl, carboxyalkyl, aryl, sulfo, and formyl, alone or in combination. Furthermore, the substituents on the fluorophore are in some cases further modified to provide chemically reactive functional groups. The subsequent modifications include but are not limited to chemically reactive derivatives of carboxylic acids such as succinimidyl esters, anhydrides, sulfonyl halides, amine and hydrazine derivatives, alcohols, haloacetamides, and isocyanates. Several examples of derivatives that have the properties claimed by this invention and the precursors that are used in their synthesis are listed in Tables 1 to 3.

TABLE 1
EXAMPLES OF SUBSTITUENTS OF NEW DIPYRROMETHENEBORON DIFLUORIDE DYES

| # | $R_3$ | $R_2$ | $R_1$ | $R_6$ | $R_5$ | $R_4$ |
|---|---|---|---|---|---|---|
| 1 | $CH_3$ | $CH_2CH_2CO_2C_2H_5$ | $CH_3$ | $CH_3$ | H | $CH_3$ |
| 2 | $CH_3$ | $CH_2CH_2CO_2H$ | $CH_3$ | $CH_3$ | H | $CH_3$ |
| 3 | $CH_3$ | $CH_2CH_2CO_2Succ^*$ | $CH_3$ | $CH_3$ | H | $CH_3$ |
| 4 | $CH_3$ | $CH_2CH_2CO_2C_2H_5$ | $CH_3$ | $CH_3$ | $C_2H_5$ | $CH_3$ |
| 5 | $CH_3$ | $CH_2CH_2CO_2H$ | $CH_3$ | $CH_3$ | $C_2H_5$ | $CH_3$ |
| 6 | $CH_3$ | $CH_2CH_2CO_2Succ^*$ | $CH_3$ | $CH_3$ | $C_2H_5$ | $CH_3$ |
| 7 | $CH_2CO_2CH_3$ | H | $CH_3$ | $CH_3$ | H | $CH_3$ |
| 8 | $CH_2CO_2H$ | H | $CH_3$ | $CH_3$ | H | $CH_3$ |
| 9 | $CH_2CO_2Succ^*$ | H | $CH_3$ | $CH_3$ | H | $CH_3$ |
| 10 | $CH_3$ | $CH_2CH_2CO_2CH_3$ | $CH_3$ | $CH_3$ | H | H |
| 11 | $CH_3$ | $CH_2CH_2CO_2H$ | $CH_3$ | $CH_3$ | H | H |
| 12 | $CH_2CO_2CH_3$ | H | $CH_3$ | $CH_3$ | H | H |
| 13 | $CH_3$ | $CH_2CH_2CO_2C_2H_5$ | $CH_3$ | H | H | H |
| 14 | $CH_3$ | $SO_2Cl$ | $CH_3$ | $CH_3$ | H | H |
| 15 | $CH_3$ | $CH_2CH_2C(=O)NHNH_2$ | $CH_3$ | $CH_3$ | H | $CH_3$ |
| 16 | $CH_3$ | $CH_2CH_2C(=O)NH_3$ | $CH_3$ | $CH_3$ | H | $CH_3$ |
| 17 | $CH_3$ | $CH_2CH_2N=C=O$ | $CH_3$ | $CH_3$ | H | $CH_3$ |
| 18 | $CH_3$ | $CH_2CH_2C(=O)-NH(CH_2)_5NH_2$ | $CH_3$ | $CH_3$ | H | $CH_3$ |
| 19 | $CH_3$ | $CH_2CH_2C(=O)-NH(CH_2)_5NHC(=O)-CH_2I$ | $CH_3$ | $CH_3$ | H | $CH_3$ |
| 20 | $CH_3$ | $CH_2CH_2C(=O)-O-C(=O)O-CH_2CH_3$ | $CH_3$ | $CH_3$ | H | $CH_3$ |
| 21 | $CH_3$ | $CH=O$ | $CH_3$ | $CH_3$ | H | $CH_3$ |
| 22 | $CH_3$ | $CH_2OH$ | $CH_3$ | $CH_3$ | H | $CH_3$ |
| 23 | $CH_3$ | $SO_2F$ | $CH_3$ | $CH_3$ | H | $CH_3$ |
| 24 | $CH_3$ | $SO_2NHNH_2$ | $CH_3$ | $CH_3$ | H | $CH_3$ |
| 25 | $CH_3$ | $CH_2CH_2NHC(=O)-O-CH_2CH_3$ | $CH_3$ | $CH_3$ | H | $CH_3$ |
| 26 | $CH_3$ | H | $CH_3$ | $C_6H_5$ | H | $C_6H_5$ |
| 27 | $CH_3$ | H | ** | $CH_3$ | H | $CH_3$ |
| 28 | $CH_3$ | Br | $CH_3$ | $CH_3$ | H | $CH_3$ |
| 29 | $CH_3$ | Br | $CH_3$ | $CH_3$ | Br | $CH_3$ |
| 30 | $CH_3$ | $CH_2CH_2NH_2$ | $CH_3$ | $CH_3$ | H | $CH_3$ |
| 31 | $CH_3$ | $CH_2CH_2C(=O)-NH-(CH_2)_5NHC(=O)CF_3$ | $CH_3$ | $CH_3$ | H | $CH_3$ |

TABLE 1-continued
EXAMPLES OF SUBSTITUENTS OF NEW DIPYRROMETHENEBORON DIFLUORIDE DYES

| # | R$_3$ | R$_2$ | R$_1$ | R$_6$ | R$_5$ | R$_4$ |
|---|---|---|---|---|---|---|
| 32 | CH$_3$ | SO$_3$Na | CH$_3$ | CH$_3$ | H | CH$_3$ |
| 33 | CH$_3$ | H | CH$_3$ | CH$_3$ | H | CH$_3$ |

*Succ = succinimidyl ester
**Substituent = CH=CH—(p)-C$_6$H$_4$—N(CH$_3$)$_2$
R$_7$ is hydrogen in all of the structures listed.

TABLE 2
PYRROLE INTERMEDIATES

| # | R$_1$ | R$_2$ | R$_3$ | R$_4$ |
|---|---|---|---|---|
| 34 | CH$_3$ | CH$_2$CH$_2$C(=O)OCH$_2$CH$_3$ | CH$_3$ | C(=O)OCH$_2$CH$_3$ |
| 35 | CH$_3$ | CH$_2$CH$_2$C(=O)OCH$_2$CH$_3$ | CH$_3$ | H |
| 36 | C(=O)OC$_2$H$_5$ | CH$_2$C(=O)OCH$_3$ | H | CH$_3$ |
| 37 | H | CH$_2$C(=O)OCH$_3$ | H | CH$_3$ |
| 38 | C$_6$H$_5$ | H | C$_6$H$_5$ | H |
| 39 | CH=O | H | H | H |
| 40 | CH=O | H | H | CH$_3$ |
| 41 | CH=O | CH$_3$ | H | CH$_3$ |
| 42 | CH=O | CH$_3$ | CH$_2$CH$_3$ | CH$_3$ |

TABLE 3
DIPYRROMETHENE INTERMEDIATES

| # | R$_1$ | R$_2$ | R$_3$ | R$_4$ | R$_5$ | R$_6$ |
|---|---|---|---|---|---|---|
| 43 | CH$_3$ | CH$_2$CH$_2$C(=O)OC$_2$H$_5$ | CH$_3$ | CH$_3$ | H | CH$_3$ |
| 44 | CH$_3$ | H | CH$_2$C(=O)OCH$_3$ | CH$_3$ | H | CH$_3$ |
| 45 | CH$_3$ | H | CH$_3$ | C$_6$H$_5$ | H | C$_6$H$_5$ |
| 46 | CH$_3$ | CH$_2$CH$_2$C(=O)OC$_2$H$_5$ | CH$_3$ | CH$_3$ | C$_2$H$_5$ | CH$_3$ |
| 47 | CH$_3$ | CH$_2$CH$_2$C(=O)OC$_2$H$_5$ | CH$_3$ | H | H | CH$_3$ |
| 48 | CH$_3$ | CH$_2$CH$_2$C(=O)OC$_2$H$_5$ | CH$_3$ | H | H | H |

Chemically reactive derivatives of fluorophores have wide utility as tracers. This invention describes methods for preparation of dipyrrometheneboron difluoride dyes that incorporate carboxylic acids, sulfonic acids and aldehydes and their subsequent modification to give chemically reactive reagents that can be coupled to other molecules for use as fluorescent tracers. The reactive functional groups of the dipyrrometheneboron difluoride dyes that have been prepared and the functional groups with which they are most reactive are listed in Table 4. The tabulation is not meant to be inclusive of chemical reactivity since with the appropriate choice of solvent, temperature and catalysts, other functional groups can be made to react.

TABLE 4

| REACTIVE FUNCTION | REACTIVE SITES |
|---|---|
| succinimidyl esters | amines, thiols |
| anhydrides | amines, alcohols |
| acyl azides | amines |
| isocyanates | amines, thiols, alcohols, phenols |

TABLE 4-continued

| REACTIVE FUNCTION | REACTIVE SITES |
|---|---|
| sulfonyl chlorides | amines, phenols, alcohols |
| sulfonyl fluorides | active sites of esterases |
| hydrazines | aldehydes, ketones, acid derivative |
| amines | carboxylic acids, aldehydes and ketones |
| haloacetamides | thiols, imidazoles, phenols, amines |
| alcohols | acid derivatives |

Emission spectra of chemical 8 from Table 1 versus fluorescein is given in FIG. 1. Obvious is the similar wavelength for maximum emission but significantly narrower spectral width of the dipyrrometheneboron difluoride dye. The narrower spectral width makes the dyes valuable for applications requiring multiple dyes such as flow cytometry and DNA sequencing. The extinction coefficients for the dipyrrometheneboron difluoride dyes are generally greater than 50,000 cm$^{-1}$ M$^{-1}$ and the quantum yields of the dyes (except 21, 27, 28, and 29) are generally above 0.5. The dyes show only minor spectral shifts and intensity changes between water, methanol and chloroform and have absorption and emission spectra that lack significant pH dependence between pH 3 and 10. Table 5 lists the approximate spectral properties of several of the dyes that are the subject of this invention.

EXPERIMENTAL

The following synthetic schemes illustrate how one skilled in the art could synthesize a variety of chemically reactive derivatives containing the desired fluorophore that are the subject of this invention. The methods outlined are intended to be illustrative and not to define or limit the possible methods of dye synthesis. Inclusion of spectral and other characterization of some of the synthetic products and intermediates in Tables 5 and 6 is intended to facilitate comparison and confirmation of products by one skilled in interpretation of spectral techniques and not to specifically define limitations or absolute values for physical properties of the materials.

The general scheme for synthesis of dipyrrometheneboron difluoride dyes that can be modified to have the desired chemical reactivity falling within the scope of this patent is illustrated in FIG. 2. The general method consists of an acid catalyzed condensation of a 2-acylpyrrole or appropriately substituted 2-acylpyrrole with pyrrole or a substituted pyrrole having a hydrogen on the 2-position (Table 2) to give a dipyrromethene intermediate (Table 3). Frequently there are two alternative routes whose choice depends primarily on the availability or ease of synthesis of the acyl pyrrole reactants. The dipyrromethene intermediate is condensed with borontrifluoride or a complex of boron trifluoride such as its etherate in the presence of a base to give the heterocyclic dye. Suitable bases include but are not limited to trimethylamine, triethylamine, tetramethylethylenediamine, and diazobicycloundecene. Suitable substitutents on the pyrroles include but are not limited to hydrogen, alkyl, cycloalkyl, aryl, arylalkyl and acyl. Dipyrrometheneboron difluoride products may be modified in a subsequent reaction by chemical techniques known to one skilled in the art including but not limited to sulfonation, nitration, alkylation, acylation, and halogenation. Furthermore, the substituents can in some cases be further modified to introduce chemically reactive functional groups that are understood to fall within the scope of this patent. Examples of methods that are suitable for preparation of selected members of this new class of reactive dyes are given in the schemes outlined below. It is recognized that variations in the synthetic methods and reactants are possible that would fall within the scope and intent of this patent.

TABLE 5

PHYSICAL PROPERTIES OF NEW DIPYRROMETHENEBORON DIFLUORIDE DYES

| # | M.P. (°C.) | ABS$_{max}$ (nm) | EM$_{max}$ (nm) | SOLVENT | R$_f$ | T.L.C. SOLVENT |
|---|---|---|---|---|---|---|
| 1 | 127–128 | 510.0 | 522.0 | methanol | 0.55 | MeOH:CHCl$_3$ (1:99) |
| 2 | 155–157 | 512.4 | 522.0 | methanol | 0.58 | MeOH:CHCl$_3$ |
| 3 | 151 (dec) | 514.8 | 522.0 | chloroform | 0.49 | EtOAc:CHCl$_3$ |
| 4 | 105–106 | 522.4 | 534.0 | methanol | 0.58 | MeOH:CHCl$_3$ (1:99) |
| 5 | 145–148 | 524.0 | 534.0 | methanol | 0.62 | MeOH:CHCl$_3$ |
| 6 | 155 (dec) | 526.8 | 536.0 | chloroform | 0.54 | EtOAc:CHCl$_3$ |
| 7 | 165–166 | 502.4 | 514.0 | methanol | 0.58 | MeOH:CHCl$_3$ (1:99) |
| 8 | 167–170 | 502.4 | 514.0 | methanol | 0.26 | MeOH:CHCl$_3$ |
| 9 | 162 (dec) | 510.0 | 519.0 | chloroform | 0.44 | EtOAc:CHCl$_3$ |
| 10 | 77–78 | 510.4 | 521.0 | methanol | 0.61 | EtOAc:CHCl$_3$ |
| 11 | 147–149 | 512.4 | 523.0 | methanol | 0.53 | MeOH:CHCl$_3$ |
| 12 | 94–95 | 504.8 | 515.0 | methanol | 0.58 | MeOH:CHCl$_3$ (1:99) |
| 13 | 55–56 | 501.2 | 516.0 | methanol | 0.56 | MeOH:CHCl$_3$ (1:99) |
| 14 | 150 (dec) | 482.0 | 506.0 | chloroform | 0.55 | CHCl$_3$ |
| 15 | 210–212 | 510.4 | 521 | methanol | 0.39 | MeOH:CHCl$_3$ (1:99) |
| 16 | 135–137 | 514.8 | 523 | chloroform | 0.53 | CHCl$_3$ |
| 19 | 72 (dec) | 511.2 | 520 | methanol* | 0.50 | MeOH:CHCl$_3$ (1:99) |
| 20 | 125–126 | 516.4 | 525 | chloroform | 0.27 | CHCl$_3$ |
| 21 | 245 (dec) | 489.6 | 513 | methanol | 0.62 | EtOAc |
| 22 | 190 (dec) | 504.4 | 515 | methanol | 0.49 | EtOAc |
| 23 | 200 (dec) | 476.6 | 504 | chloroform | 0.47 | CHCl$_3$ |
| 24 | 195 (dec) | 490.4 | 505 | chloroform | 0.56 | MeOH:CHCl$_3$ (1:9) |
| 25 | 115–116 | 516.4 | 525 | chloroform | 0.54 | MeOH:CHCl$_3$ (3:97) |
| 26 | 225–228 | 524.8 | 547 | chloroform | 0.60 | chloroform |
| 27 | 270 (dec) | 607.6 | 652 | chloroform | 0.36 | chloroform |
| 28 | 215 (dec) | 516.8 | 531 | chloroform | 0.56 | chloroform |
| 29 | 230 (dec) | 534.0 | 548 | chloroform | 0.71 | chloroform |
| 30 | 147 (dec) | 517.6 | 526 | chloroform | 0.22 | MeOH:AcOH:CHCl$_3$ |

TABLE 5-continued
PHYSICAL PROPERTIES OF NEW DIPYRROMETHENEBORON DIFLUORIDE DYES

| # | M.P. (°C.) | ABS$_{max}$ (nm) | EM$_{max}$ (nm) | SOLVENT | R$_f$ | T.L.C. SOLVENT (15:1:100) |
|---|---|---|---|---|---|---|

*containing 1% 2-mercaptoethanol

TABLE 6
$^1$H—NMR SPECTRAL DATA OF DIPYRROMETHENEBORON DIFLUORIDE DYES

| # | Chemical shift in ppm in CDCl$_3$ (300 MHz NMR) |
|---|---|
| 1 | 1.25 (t,3H,CH$_3$), 2.20 (s,3H,CH$_3$), 2.24 (s,3H,CH$_3$), 2.44 (t,2H,CH$_2$), 2.52 (s,2 × 3H,2 × CH$_3$), 2.72 (t,2H,CH$_2$), 4.13 (q,2H,CH$_2$), 6.03(s,1H,ArH) 7.01 (s,1H,=CH) |
| 2 | 2.22 (s,3H,CH$_3$), 2.26 (s,3H,CH$_3$), 2.46 (t,2H,CH$_2$), 2.54 (s,2 × 3H,2 × CH$_3$) 2.75 (t,2H,CH$_2$), 6.05 (s,1H,ArH), 7.04 (s,1H,ArH) |
| 3 | 2.22 (s,3H,CH$_3$), 2.25 (s,3H,CH$_3$), 2.53 (s,2 × 3H,2 × CH$_3$), 2.74 (t,2H,CH$_2$) 2.77 (t,2H,CH$_2$), 2.86 (s,4H,CH$_2$), 6.05 (s,1H,ArH), 7.04 (s,1H,=CH) |
| 4 | 1.08 (t,3H,CH$_3$), 1.25 (t,3H,CH$_3$), 2.17 (s,3H,CH$_3$), 2.19 (s,3H,CH$_3$), 2.39 (q,2H,CH$_2$), 2.44 (t,2H,CH$_2$), 2.51 (s,3H,CH$_3$), 2.72 (t,2H,CH$_2$), 4.14 (q,2H,CH$_2$), 6.97 (s,1H,=CH$_2$) |
| 5 | 1.06 (t,3H,CH$_3$), 2.17 (s,3H,CH$_3$), 2.19 (s,3H,CH$_3$), 2.40 (q,2H,CH$_2$), 2.50 (s,2 × 3H,2 × CH$_3$), 2.72 (t,2H,CH$_2$), 2.83 (t,2H,CH$_2$), 6.96 (s,1H,=CH) |
| 6 | 1.07 (t,3H,CH$_3$), 2.18 (s,3H,CH$_3$), 2.20 (s,3H,CH$_3$), 2.40 (q,2H,CH$_2$), 2.51 (s,2 × 3H,2 × CH$_3$), 2.73 (t,2H,CH$_2$), 2.83 (t,2H,CH$_2$), 2.86 (s,4H,CH$_2$), 7.09 (s,1H,=CH) |
| 7 | 2.27 (s,3H,CH$_3$), 2.56 (s,2 × 3H,2 × CH$_3$), 3.63 (s,2H,CH$_2$), 3.72 (s,3H,CH$_3$) 6.10 (s,1H,ArH), 6.25 (s,1H,ArH), 7.11 (s,1H,=CH) |
| 8 | 2.27 (s,3H,CH$_3$), 2.56 (s,2 × 3H,2 × CH$_3$), 3.67 (s,2H,CH$_2$), 6.10 (s,1H,ArH) 6.25 (s,1H,ArH), 7.10 (s,1H,=CH) |
| 9 | 2.30 (s,3H,CH$_3$), 2.56 (s,2 × 3H,2 × CH$_3$), 2.86 (s,4H,CH$_2$), 3.95 (s,2H,CH$_2$) 6.12 (s,1H,ArH), 6.29 (s,1H,ArH), 7.11 (s,1H,=CH) |
| 10 | 2.18 (s,3H,CH$_3$), 2.45 (t,2H,CH$_2$), 2.55 (s,3H,CH$_3$), 2.57 (s,3H,CH$_3$), 2.2 (t,2H,CH$_2$), 3.68 (s,3H,CH$_3$), 6.19 (d,1H,ArH), 6.85 (d,1H,ArH) 7.02 (s,1H,=CH) |
| 11 | 2.20 (s,3H,CH$_3$), 2.52 (t,2H,CH$_2$), 2.54 (s,3H,CH$_3$), 2.56 (s,3H,CH$_3$), 2.77 (t,2H,CH$_2$), 6.21 (d,1H,ArH), 6.86 (d,1H,ArH), 7.04 (s,1H,=CH) |
| 12 | 2.59 (s,3H,CH$_3$), 2.61 (s,3H,CH$_3$), 3.63 (s,2H,CH$_2$), 3.73 (s,3H,CH$_3$), 6.28 (s,1H,ArH), 6.29 (d,1H,ArH), 6.94 (d,1H,ArH), 7.14 (s,1H,=CH) |
| 13 | 1.25 (t,3H,CH$_3$), 2.24 (s,3H,CH$_2$), 2.46 (t,2H,CH$_2$), 2.59 (s,3H,CH$_3$), 2.74 (t,2H,CH$_2$), 4.13 (q,2H,CH$_2$), 6.42 (d,1H,ArH), 6.92 (dd,1H,ArH), 7.17 (s,1H,=CH, 7.62 (d,1H,ArH) |
| 14 | 2.37 (s,3H,CH$_3$), 2.54 (s,3H,CH$_3$), 2.66 (s,3H,CH$_3$), 2.83 (s,3H,CH$_3$), 6.34 (s,1H,ArH), 7.23 (s,1H,=CH) |
| 15 | 2.19 (s,3H,CH$_3$), 2.25 (s,3H,CH$_3$), 2.26 (t,2H,CH$_2$), 2.51 (s,3H,CH$_3$), 2.53 (s,3H,CH$_3$), 2.76 (t,2H,CH$_2$), 3.88 (bs,2H,NH$_2$), 6.04 (s,1H,ArH), 6.70 (bs,1H,NH), 7.01 (s,1H,=CH) |
| 16 | 2.23 (s,3H CH$_3$), 2.26 (s,3H,CH$_3$), 2.53 (s,3H,CH$_3$), 2.54 (s,3H,CH$_3$), 2.71 (t,2H,CH$_2$), 3.38 (t,2H,CH$_2$), 6.06 (s,1H,ArH), 7.05 (s,1H,=CH) |
| 19 | 1.25 to 1.85 (m.8H,4 × CH$_2$), 2.20 (s,3H,CH$_3$), 2.25 (s,3H,CH$_3$), 2.32 (t,2H,CH$_2$), 2.52 (s,6H,2 × CH$_3$), 2.76 (t,2H,CH$_2$), 3.21 (dt,4H,2 × CH$_2$), 3.66 (s,2H,CH$_2$I), 5.63 (t,1H,NH), 6.04 (s,1H,ArH), 6.32 (t,1H,NH), 7.02 (s,1H,=CH) |
| 20 | 1.25 (t,3H,CH$_3$), 2.20 (s,3H,CH$_3$), 2.24 (s,3H,CH$_3$), 2.43 (t,2H,CH$_2$), 2.52 (s,6H,2 × CH$_3$), 2.72 (t,2H,CH$_2$), 4.13 (q,2H,CH$_2$), 6.03 (s,1H,ArH), 7.01 (s,1H,=CH) |
| 21 | 2.32 (s,3H,CH$_3$), 2.52 (s,3H,CH$_3$), 2.60 (s,3H,CH$_3$), 2.79 (s,3H,CH$_3$), 6.23 (s,1H,ArH), 7.21 (s,1H,=CH), 10.07 (s,1H,CH=O) |
| 22 | 2.26 (s,3H,CH$_3$), 2.29 (s,3H,CH$_3$), 2.52 (s,3H,CH$_3$), 2.56 (s,3H,CH$_3$), 4.51 (s,2H,CH$_2$), 6.08 (s,1H,ArH), 7.08 (s,1H,=CH) |
| 23 | 2.35 (s,3H,CH$_3$), 2.49 (s,3H,CH$_3$), 2.64 (s,3H,CH$_3$), 2.77 (s,3H,CH$_3$), 6.32 (s,1H,ArH), 7.25 (s,1H,=CH) |
| 24 | 1.60 (bs,2H NH$_2$), 2.34 (s,3H CH$_3$), 2.48 (s,3H,CH$_3$), 2.61 (s,3H,CH$_3$), 2.77 (s,3H,CH$_3$), 5.47 (s,1H,NH), 6.27 (s,1H,ArH), 7.23 (s,1H,=CH) |
| 25 | 1.25 (t,3H,CH$_3$), 2.20 (s,3H,CH$_3$), 2.25 (s,3H,CH$_3$), 2.52 (s,3H,CH$_3$), 2.53 (s,3H,CH$_3$), 2.60 (t,2H,CH$_2$), 3.24 (dt,2H,CH$_2$), 4.12 (q,2H,CH$_2$), 4.72 (t,1H,NH), 6.04 (s,1H,ArH), 7.03 (s,1H,=CH) |
| 26 | 2.28 (s,3H,CH$_3$), 2.58 (s,3H,CH$_3$), 6.16 (s,1H,ArH), 6.68 (s,1H,ArH), 7.26 (s,1H,=CH), 7.48 (t,4H,ArH), 7.53 (t,2H,ArH), 7.95 (d,4H,ArH) |
| 27 | 2.25 (s,3H,CH$_3$), 2.28 (s,3H,CH$_3$), 2.57 (s,3H,CH$_3$), 3.03 (s,6H,NMe$_2$), 6.03 (s,1H,ArH), 6.67 (s,1H,ArH), 6.68 (d,2H,ArH), 6.95 (s,1H,ArH), 7.23 (d,1H,=CH), 7.43 (d,1H,=CH), 7.50 (d,2H,ArH) |
| 28 | 2.22 (s,3H,CH$_3$), 2.26 (s,3H,CH$_3$), 2.55 (s,6H,2 × CH$_3$), 6.10 (s,1H,ArH), 7.05 (s,1H,=CH) |
| 29 | 2.23 (s,6H,2 × CH$_3$), 2.56 (s,6H,2 × CH$_3$), 7.08 (s,1H,=CH) |
| 30 | 2.18 (s,3H,CH$_3$), 2.22 (s,3H,CH$_3$), 2.30 (t,2H,CH$_2$), 2.53 (s,6H,2 × CH$_3$), 2.52–2.65 (m,2H,CH$_2$), 2.83 (t,2H,NH$_2$), 6.04 (s,1H,ArH), |

TABLE 6-continued
¹H—NMR SPECTRAL DATA OF DIPYRROMETHENEBORON DIFLUORIDE DYES

| # | Chemical shift in ppm in CDCl₃ (300 MHz NMR) |
|---|---|
| | 7.02 (s, 1H.=CH) |

I. Ethyl 2,4-dimethyl-3-pyrrolepropionate, 35

In a 1000 ml three-necked, round bottom flask, fitted with a thermometer and a nitrogen inlet, was placed 50 ml of 85% phosphoric acid. The mixture was heated to 120° C. under a nitrogen atmosphere. Into this solution was added dropwise over a period of one hour 19.4 g (72.6 mmol) of ethyl 2,4-dimethyl-5-(ethoxycarbonyl)-3-pyrrolepropionate 34 with vigorous stirring. After heating the reaction mixture an additional hour at 120° C., it was cooled to room temperature and 200 ml of distilled water was added. This was partially neutralized by the slow addition of 2M sodium hydroxide while the mixture was stirred vigorously in an ice bath. Extraction of the aqueous phase with two 250 ml portions of chloroform, followed by drying of the organic phase with anhydrous sodium sulfate and evaporation of the solvent under reduced pressure gave a brown solid. Part of the ethyl ester was lost from the propionic acid during decarboxylation. The crude brown solid was dissolved in 150 ml absolute ethanol in a 250 ml round bottom flask and 0.5 g of p-toluenesulfonic acid was added. After the solution was heated under reflux for 36 hours in a nitrogen atmosphere, ethanol was distilled off under reduced pressure. The resulting residue was treated with 300 ml of chloroform, washed twice with saturated sodium bicarbonate and once with water. The organic phase was dried over sodium sulfate and evaporated under reduced pressure to give a brown oil. Distillation (120° C., 0.1 mm Hg) of the crude product gave 10.5 g (74%) of a colorless oil which solidified on standing to give needles, m.p. 37° C. (literature 37.5° C.).

II. 4-(2-ethoxycarbonyl)ethyl-3,5,3',5'-tetramethyl-dipyrromethene, hydrobromide, 43

To a solution of 4.30 g (34.9 mmol) of 2,4-dimethyl-pyrrole-5-carboxaldehyde, 41, and 6.80 g (34.8 mmol) of ethyl 2,4-dimethyl-3-pyrrolepropionate, 35, in 70 ml ethanol was added 6.0 ml (54.1 mmol) of 48% hydrobromic acid while the reaction was stirred vigorously in an ice bath. After stirring in an ice bath for 1 hour, the resulting orange precipitate was collected by filtration and washed with 10 ml of ethanol. It was dried under vacuum to give 11.8 g (89%) of an orange powdery solid as a crude product. This was used in the next step without further purification. The other pyrromethene dyes in Table 3 were prepared in a similar manner.

III. 4,4-difluoro-2-(2-(ethoxycarbonylethyl)-1,3,5,7-tetramethyl-4-bora-3a,4a-diaza-s-indacene, 1

To a suspension of 3.70 g (9.70 mmol) of 4-(2-ethoxycarbonyl)ethyl-3,5,3',5'-tetramethyldipyrromethene hydrobromide, 43, in 450 ml of dry benzene was added 7.40 g (48.6 mmol) of 1,8-diazabicyclo[5.4.0]undec-7-ene, followed by addition of 2.88 g (20.3 mmol) of boron trifluoride etherate. After the mixture was stirred at room temperature for 20 minutes, it was washed with three 400 ml portions of water. The organic layer was separated, dried over anhydrous sodium sulfate and concentrated under reduced pressure to give a brown solid. The crude product was purified by chromatography on silica gel with chloroform as eluant to give 680 mg (21%) of an orange red solid.

IV. 4,4-difluoro-2-(2-carboxyethyl)-1,3,5,7-tetramethyl-4-bora-3a,4a-diaza-s-indacene, 2

To a solution of 650 mg (1.86 mmol) of 1, in 150 ml of methanol was added a solution of 510 mg (3.69 mmol) of potassium carbonate in 30 ml of water. The mixture was stirred at room temperature for 3 days. The reaction mixture was concentrated to a volume of about 20 ml under reduced pressure to remove most of the methanol. The resulting mixture was diluted with 50 ml of water and extracted with 50 ml of chloroform to remove unreated starting material. The aqueous layer was separated and carefully acidified to pH 2-3 by dropwise addition of 0.1N solution of hydrochloric acid while the mixture was stirred in an ice bath. Extraction of the aqueous phase with chloroform followed by drying of the organic phase with anhydrous sodium sulfate and concentration under reduced pressure gave 510 mg (85%) of the desired product.

V. Ethyl 5-carbomethoxy-4-carbomethoxymethyl-2-methylpyrrole-3-carboxylate, 36

To a stirred and ice-cold solution of 17.5 g (0.10 mol) of dimethylacetone dicarboxylate in 80 ml of acetic acid was added a solution of 6.9 g (0.10 mol) sodium nitrite in 10 ml water at such a rate that the temperature remained below 10° C. After the addition was complete, the reaction mixture was stirred at ice bath temmperature for 1.5 hours and then set aside at room temperature for 16 hours. It was then added during 40 minutes into a vigorously stirred mixture of 16.0 g (0.21 mol) ammonium acetate, 13.1 g (0.10 mol) of ethyl acetoacetate, 50 ml of glacial acetic acid and 7.5 g zinc dust in a 1000 ml flask while cooling in ice water. During the addition an additional 15.0 g of zinc dust was added in small portions and the temperature of the exothermic reaction kept at 60°-65° C. The cooling bath was removed and the mixture heated at 90° C. for 2 hours. The hot solution was decanted from zinc into 1300 ml of well stirred ice water. The resulting colorless precipitate was collected by filtration, washed several times with water and dried to give 14.0 g (49%) of the desired product 36. Preparation of a similar compound, benzyl 5-carbethoxy-4-carbethoxymethyl-2-methylpyrrole-3-carboxylate is described in S. F. MacDonald, J. Chem. Soc. 4176 (1952).

VI. Methyl 5-methyl-3-pyrroleacetate, 37

A sample of 8.0 g (28 mmol) of ethyl-5-carbomethoxy-4-carbomethoxymethyl-2-methylpyrrole-3-carboxylate, 36, in 25 ml of 85% phosphoric acid was allowed to decarboxylate and worked up in the same manner as described for the preparation of ethyl 2,4-dimethyl-3-pyrrolepropionate, 35. Vacuum distillation (120° C., 0.1 mm Hg) of the crude product gave 2.15 g (50%) of a colorless oil.

The pyrromethene intermediates 44 (from 41 and 37), 45 (from 41 and 38), 46 (from 35 and 42), 47 (from 35 and 40) and 48 (from 35 and 39) were prepared by methods similar to those used to prepare 43. The dipyrrometheneboron difluoride fluorophores 4, 7, 10, 13, and 26 were prepared from the pyrromethene intermediates 46, 44, 47, 48, and 45 respectively by the method used to prepare 1 from 43. Hydrolysis of the esters to the free acids was done by the method used to convert 1 to 2 and conversion of these to other reactive derivatives was accomplished my reactions similar to those used to convert 1 to the reactive derivatives described below.

Pyrrole-2-carboxaldehydes needed for the synthesis of pyrrolomethenes were either commercially available or readily prepared from the corresponding pyrroles by the Vilsmeyer Haak formylation. Ref: R. M. silverstein, E. E. Ryskiewicz and C. Willard. Org. Synth. Coll Vol IV, page 831.

2,4-Dimethylpyrrole was prepared by decarboxylation of 2,4-dimethyl-3,5-dicarbethoxypyrrole. [A. Treibs, L. Schulze. Ann. der Chemie 739, 225 (1970)].

2-Methylpyrrole was prepared from pyrrole-2-carboxaldehyde by reduction with $LiAlH_4$. [R. L. Hinman and S. Theodoropulus. J. Org. Chem. 28, 3052 (1963)].

VII. Further halogenation of dipyrrometheneboron difluoride dyes as demonstrated by the preparation of mono and dibromo dyes 28 and 29

A mixture of 10 mg 4,4-difluoro-1,3,5,7-tetramethyl-4-bora-3a,4a-diaza-s-indacene 33, 8 mg of N-bromosuccinimide and a few particles of benzoyl peroxide in 10 ml carbon tetrachloride was heated under reflux for 13 hours. By TLC, all of the starting material was shown to be consumed. Succinimide was removed by filtration and the reaction mixture purified by column chromatography to yield 3 mg of the monobromo derivative 28 and 5 mg of the dibromo derivative 29. The same chemistry can be applied to other reactive dipyrrometheneboron difluoride intermediates possessing hydrogen substituted aromatic positions.

VIII. Further modification of the dipyrrometheneboron difluoride fluorophore by condensation with aromatic aldehydes as demonstrated by preparation of styrene dye 27

A mixture of 30 mg 33, 25 mg p-dimethylaminobenzaldehyde and 9 drops of piperidine in 2 ml isopropyl alcohol was heated at reflux for 16 hours. After evaporation, the blue solid was purified by silica gel column chromatography with elution by a mixture of chloroform and hexanes (1:1). The major fractions were combined and evaporated to yield 32 mg (70%) of the dark blue solid 27.

IX. Succinimidyl esters 3, 6, and 9

To a solution of 120 mg (0.37 mmol) 2 in 10 ml of ethyl acetate was added 43 mg (0.37 mmol) N-hydroxysuccinimide followed by addition of 85 mg (0.41 mmol) N,N'-dicyclohexylcarbodiimide. The mixture was stirred at room temperature for 24 hours. The N,N'-dicyclohexylurea which formed was removed by filtration and the filtrate was evaporated to dryness under reduced pressure to give an orange-red solid. It was purified by chromatography on silica gel with chloroform as eluant to give 118 mg (77%) of orange-red needles of 3. Succinimidyl esters 6 and 9 were prepared by similar procedures.

X. Mixed anhydride 20

To a solution of 20 mg 2 in 0.5 ml methylene chloride was added 100 μl triethylamine followed by addition of 100 μl ethyl chloroformate. The mixture was stirred at room temperature for 16 hours then evaporated. The product was eluted from a silica gel column with chloroform yielding 19 mg (78%) of a yellow solid.

XI. Hydrazide 15

Ester 1, 100 mg was stirred in methanol solution with 250 μl anhydrous hydrazine. After standing at room temperature for three days, the reaction mixture was evaporated then chromatographed on silica gel with 10% methanol in chloroform. The yield of hydrazide product was 61 mg (67%). 25 mg of unreacted 1 was recovered from the column. Thin layer chromatography showed the product to react quantitatively with acetone to give the hydrazone.

XII. Azide 16

A sample of 20 mg of the hydrazide 15 was dissolved in 7 ml of 0.1M hydrochloric acid and this solution stirred in an ice bath. A solution of 10 mg sodium nitrite in 0.5 ml water was added and then stirred at ice bath temperature for 30 minutes. The resulting solid was collected by filtration. The crude product was purified by silica gel column chromatography with chloroform elution to yield 17 mg of the azide 16 (82%).

XIII. Isocyanate 17 and urethane 25

Rearrangement of the azide to the isocyanate 17 was accomplished by refluxing a solution of 10 mg of 16 in 1 ml of toluene for 1 hour. Without isolation the product was characterized as its ethyl urethane by adding a few drop of anhydrous ethanol to the refluxing toluene solution for 30 minutes. The crude solid isolated by evaporation of the reaction mixture was purified by column chromatography on silica gel with chloroform:methanol (97:3) elution yielding 10 mg (94%) of the urethane 25.

XIV. Amine 30

To a solution of 20 mg of the azide 16 in 2 ml glacial acetic acid was added 0.5 ml water. After heating at reflux for 1 hour, the reaction mixture was concentrated under reduced pressure. The resulting crude product was purified by preparative thin layer chromatography with 30% methanol in chloroform as eluant. The ninhydrin-positive major band was eluted from the silica gel with chloroform, washed with dilute NaOH and evaporated to yield 7 mg (42%) of the amine 30 as an orange-yellow solid.

XV. Cadaverine monoamide 18

A sample of cadaverine monotrifluoroacetamide, hydrochloride (30 mg) was suspended in 5 ml chloroform containing 10 drops of triethylamine. After stirring a few minutes, 50 mg of the succinimidyl ester 3 in 1 ml chloroform was added. After stirring 1 hour at room temperature, most of the succinimidyl ester was consumed. The reaction was concentrated and the residue subjected to column chromatography to give 60 mg (100%) of the protected amine 31.

To a solution of 58 mg of the trifluoroacetamide, 31, in 5 ml methanol was added 80 mg potassium carbonate in 1 ml water. The solution was stirred 3 days at room temperature then then the solvent evaporated. The residue was extracted into chloroform from water then into 0.1M HCl. The aqueous extract was made basic with 0.1M NaOH and 40 mg orange brown crystals collected. The product was demonstrated by thin layer chromatography to be ninhydrin positive and to react with acetic anhydride to give a new product.

XVI. Iodoacetamide 19

Cadaverine 18, 20 mg in 2 ml chloroform was mixed with 30 mg p-nitrophenyl iodoacetate for 1 hour at room temperature. After evaporation under reduced pressure, the product was purified by silica gel column chromatography to yield a major fraction with 15 mg of pure product (45%).

XVII. Reaction of iodoacetamide 19 with 2-mercaptoethanol

To a solution of one drop 2-mercaptoethanol and a few mg of sodium acetate in 0.5 ml methanol was added 1 mg of iodoacetamide 19. After 60 minutes at room temperature the starting material was consumed and a new product of lower mobility on thin layer chromatography was quantitatively formed.

XVIII. Sulfonyl chloride 14

To 5 ml of thionyl chloride was added 0.5 ml of dry dimethylformamide and the mixture stirred at room temperature for 20 minutes. To the above mixture was added 200 mg (0.57 mmol) of the sodium salt of 4,4-difluoro-2-sulfonato-1,3,5,7-tetramethyl-4-bora-3a,4a-diaza-s-indacene, 32, and the suspension was stirred at room temperature for 21 hours. After concentrating under reduced pressure, the resulting red-brown solid was treated with 50 ml of chloroform. It was poured into 50 ml of ice water and shaken vigorously for a few minutes. After transferring to a separatory funnel, the chloroform layer was extracted with three 30 ml portions of chloroform. The combined chloroform layer were washed twice with 50 ml of water. The organic phase was dried over anhydrous sodium sulfate and concentrated under reduced pressure to give a red brown solid. The crude product was further purified by chromatography on silica gel with chloroform as eluant to give 130 mg (67%) of the desired product. The starting material, 32, was obtained from 33 using the method of Vos de Wael, et al. (1985).

XIX. Sulfonyl fluoride 23

To a slurry of 10 mg of the sulfonyl chloride 14 in 1 ml acetone was added a solution of 10 mg potassium fluoride in 0.2 ml water and the mixture stirred at room temperature for 4 hours. The mixture was distributed between water and chloroform. The organic layer was separated, dried over anhydrous sodium sulfate and evaporated to dryness to give a red-brown solid. The crude product was purified by silica gel column chromatography to yield 8 mg (84%) of 23. The sulfonyl fluoride was distinguished from the sulfonyl chloride by thin layer chromatography, melting point, absorption spectra and NMR spectrum.

XX. Sulfonyl hydrazide 24

To a solution of 10 mg of the sulfonyl chloride 14 in 200 μl chloroform was added one drop anhydrous hydrazine. After stirring 30 minutes at room temperature, TLC showed most of the starting material to be consumed. The reaction mixture was evaporated and the product purified by silica gel column chromatography to yield an orange-brown solid, 9.0 mg (91%) which was shown by TLC to react quantitatively with acetone to yield the hydrazone.

XXI. Aldehyde 21

To an ice cooled 0.5 ml dimethylformamide was added 225 μl phosphorous oxychloride while stirring under a nitrogen atmosphere. The mixture was stirred 15 minutes and then was added a solution of 500 mg 33 in 15 ml 1,2-dichloroethane while cooling in an ice bath. The reaction mixture was then heated to reflux for 15 minutes. Evolution of HCl gas was observed during this process. After cooling to room temperature a solid separated. About 30 ml chloroform was added followed by about 50 ml saturated aqueous sodium acetate. After heating at reflux for 15 minutes, the mixture was cooled and the organic layer separated, washed with aqueous sodium carbonate and dried over anhydrous sodium sulfate. Following evaporation at reduced pressure, the crude product was purified by column chromatography with chloroform elution to yield 465 mg of the pure aldehyde 21.

XXII. Alcohol 22

Reduction of 300 mg (1.09 mmol) of the aldehyde 21 in 60 ml dry tetrahydrofuran with 2.0 ml diisobutylaluminum hydride (1.0M in hexanes) at room temperature for 1 hour gave, following addition of 0.5 ml water and column purification, 220 mg (73%) alcohol 22.

XXIII. Determination of the chemical reactivity of the dyes

The chemically reactive dyes that are the subject of this invention were subjected to incubation in aqueous, methanolic, or chloroform solution with model compounds and their reactivity demonstrated by thin layer chromatography in a solvent that separated the reactive dye from its products with visual detection of the fluorescence emission. It was demonstrated that 1-aminobutane reacts to form a new product with 3, 6, 9, 14, 16, and 20, that 2-mercaptoethanol reacts with 19, that acetic anhydride reacts with 15, 18, 22, 24, and 30, that ethanol reacts with 17, that acetone reacts with 15 and 24, and that taxol reacts with 2 in the presence of N,N'-dicyclohexylcarbodimide to give an ester. Furthermore, it was demonstrated that the esters such as 1 can react with hydrazine to give hydrazines such as 15.

XXIV. Determination of the fluorescence of dipyrromethaneboron difluoride dyes

Fuorescence of the dipyrromethaneboron difluoride dyes was determined for the reactive dyes and for their conjugates with model compounds by dissolving the dye at a concentration above $1 \times 10^{-10}$M in an appropriate solvent including but not limited to water, methanol, ethanol, acetonitrile, acetone, chloroform, toluene or hexanes and measurement of the fluorscence in a suitable instrument, including but not limited to a fluorescence spectrometer, fluorescence microscope or flow cytometer. Results of the spectral determination for some of the dyes are tabulated in Table 5. Fluorescence could also be observed for the dyes in solution by visual inspection with illumination by a suitable source that gives off light at less than 530 NM.

What is claimed is:

1. Fluorescent dyes with the common structure, wherein $R_1$, $R_2$, $R_3$, $R_4$, $R_5$, and $R_6$ are chosen among the substituents hydrogen, halogen, alkyl, cycloalkyl, aryl, arylalkyl, acyl, and sulfo alone or in combination where at least one of the groups is further modified to yield a chemically reactive group capable of forming a chemical bond with a ligand.

2. Dyes according to claim 1 where the chemically reactive group is a carboxylic acid.

3. Dyes according to claim 1 where the chemically reactive group is a carboxylic acid succinimidyl ester.

4. Dyes according to claim 1 where the chemically reactive group is a carboxylic acid anhydride.

5. Dyes according to claim 1 where the chemically reactive group is sulfonyl chloride.

6. Dyes according to claim 1 where the chemically reactive group is a sulfonyl fluoride.

7. Dyes according to claim 1 where the chemically reactive group is a hydrazine derivative.

8. Dyes according to claim 1 where the chemically reactive group is an amine.

9. Dyes according to claim 1 where the chemically reactive group is an alcohol.

10. Dyes according to claim 1 where the chemically reactive group is an acyl azide.

11. Dyes according to claim 1 where the chemically reactive group is an isocyanate.

12. Dyes according to claim 1 where the chemically reactive group is a haloacetamide.

13. Dyes according to claim 1 where the chemically reactive group is an aldehyde.

* * * * *

UNITED STATES PATENT AND TRADEMARK OFFICE
CERTIFICATE OF CORRECTION

PATENT NO. : 4,774,339
DATED : September 27, 1988
INVENTOR(S) : Haugland, et al.

It is certified that error appears in the above-indentified patent and that said Letters Patent is hereby corrected as shown below:

At col 4, table 1, line 16, "$CH_2CH_2C(=O)NH_3$" should be --$CH_2CH_2C(=O)N_3$--.

At col 16, line 24, "hydrazines" should be --hydrazides--.

Signed and Sealed this

Thirtieth Day of July, 1996

Attest:

BRUCE LEHMAN

*Attesting Officer*  *Commissioner of Patents and Trademarks*